United States Patent
Grant et al.

(10) Patent No.: US 9,918,864 B2
(45) Date of Patent: Mar. 20, 2018

(54) BRACE FOR CORRECTION OF HUMERAL FRACTURES

(71) Applicant: Breg, Inc., Carlsbad, CA (US)

(72) Inventors: Gregory Grant, Phoenix, AZ (US); Jeremiah D. Schillig, Grand Prairie, TX (US)

(73) Assignee: Breg, Inc., Carlsbad, CA (US)

( * ) Notice: Subject to any disclaimer, the term of this patent is extended or adjusted under 35 U.S.C. 154(b) by 0 days.

(21) Appl. No.: 13/632,324

(22) Filed: Oct. 1, 2012

(65) Prior Publication Data
US 2013/0085433 A1    Apr. 4, 2013

Related U.S. Application Data

(60) Provisional application No. 61/542,327, filed on Oct. 3, 2011.

(51) Int. Cl.
*A61F 5/00* (2006.01)
*A61F 5/01* (2006.01)

(52) U.S. Cl.
CPC ..................... *A61F 5/013* (2013.01)

(58) Field of Classification Search
CPC ............... A61H 1/0277; A61H 1/0274; A61H 2205/06; A61H 2201/673; A61H 2201/676; A61H 2205/10; A61H 2205/102; A61H 2201/1676; A61H 2201/1673; A61F 5/01; A61F 5/0102; A61F 5/0123; A61F 5/0125; A61F 5/013; A61F 5/04; A61F 5/058; A61F 5/05858; A61F 5/37; A61F 5/3723; A61F 2005/0132; A61F 2005/0134; A61F 2005/0158; A61F 2005/0151; A61F 2005/0153; A61F 5/0585; A61F 5/05841; A61F 5/373

USPC ............... 128/846, 869, 881–882; 602/5, 16, 602/20–21, 23, 26; 601/33, 34
See application file for complete search history.

(56) References Cited

U.S. PATENT DOCUMENTS

| | | | | |
|---|---|---|---|---|
| 1,257,297 A | * | 2/1918 | Brown | 602/16 |
| 1,340,630 A | * | 5/1920 | Maddox | 602/4 |
| 2,614,558 A | * | 10/1952 | Lovell | 602/20 |
| 3,693,617 A | | 9/1972 | Trott et al. | |
| 4,237,873 A | * | 12/1980 | Terry et al. | 602/20 |

(Continued)

FOREIGN PATENT DOCUMENTS

DE    3030712 A1    3/1982

OTHER PUBLICATIONS

Sarmiento et al., "Functional Bracing of Fractures of the Shaft of the Humerus", The Journal of Bone and Joint Surgery, 1977, pp. 596-601.

(Continued)

*Primary Examiner* — Victoria J Hicks
(74) *Attorney, Agent, or Firm* — Rodney F. Brown

(57) ABSTRACT

A brace is provided for treating humeral fractures. The brace is secured to a patient's humerus and forearm. The brace utilizes a hinge system which enables the portion of the brace secured to the patient's forearm to rotate in a plurality of planes relative to the portion of the brace secured to the patient's humerus. The hinge system allows the brace to be adjusted to the most advantageous position for the patient. Once the brace has been adjusted to the most advantageous position, the hinge system can be locked so that the brace remains in that position.

29 Claims, 10 Drawing Sheets

(56) References Cited

U.S. PATENT DOCUMENTS

| | | |
|---|---|---|
| 4,320,748 A | 3/1982 | Racette et al. |
| 4,337,764 A | 7/1982 | Lerman et al. |
| 4,520,802 A | 6/1985 | Mercer et al. |
| 4,523,585 A | 6/1985 | Lamb et al. |
| 4,639,815 A | 1/1987 | Arai et al. |
| 4,662,364 A | 5/1987 | Viegas et al. |
| 4,796,611 A | 1/1989 | Wardlaw et al. |
| 4,974,583 A | 12/1990 | Freitas et al. |
| RE33,621 E | 6/1991 | Lamb et al. |
| 5,033,461 A * | 7/1991 | Young et al. ................. 602/16 |
| 5,195,944 A | 3/1993 | Schlogel et al. |
| 5,330,477 A | 7/1994 | Crook et al. |
| 5,383,844 A | 1/1995 | Munoz et al. |
| 5,407,420 A * | 4/1995 | Bastyr ................. A61F 5/05858 602/16 |
| 5,538,499 A | 7/1996 | Schwenn et al. |
| 5,662,594 A | 9/1997 | Rosenblatt |
| 5,759,165 A * | 6/1998 | Malewicz ................. 602/21 |
| 6,183,431 B1 | 2/2001 | Gach et al. |
| 6,533,741 B1 * | 3/2003 | Lee ................. A61F 5/05858 128/878 |
| 6,533,742 B1 | 3/2003 | Gach et al. |
| 6,553,741 B2 * | 4/2003 | Fantz ................. B65B 25/023 53/397 |
| 6,849,056 B1 | 2/2005 | Wiggins et al. |
| 6,953,441 B2 | 10/2005 | Goumas et al. |
| 6,991,613 B2 | 1/2006 | Sensabaugh et al. |
| 7,182,742 B2 | 2/2007 | Wardlaw et al. |
| 7,507,253 B2 | 3/2009 | Nordquist et al. |
| 7,988,653 B2 * | 8/2011 | Fout ................. A61F 5/013 24/593.1 |
| 8,292,838 B2 * | 10/2012 | Ingimundarson ..... A61F 5/0123 128/846 |
| 2002/0002348 A1 | 1/2002 | Wiggins |
| 2003/0093020 A1 | 5/2003 | Wardlaw |
| 2004/0039315 A1 | 2/2004 | Goumas |
| 2004/0073143 A1 | 4/2004 | Bonutti et al. |
| 2004/0267179 A1 * | 12/2004 | Lerman ................. A61F 5/0125 602/26 |
| 2005/0010151 A1 | 1/2005 | Sensabaugh |
| 2005/0090900 A1 | 4/2005 | Nordquist |
| 2009/0093744 A1 | 4/2009 | MacArthur |
| 2011/0112452 A1 * | 5/2011 | Schiff ................. A61F 5/0125 602/16 |
| 2012/0071802 A1 | 3/2012 | Reiley et al. |
| 2012/0303030 A1 | 11/2012 | Reiley |
| 2013/0184627 A1 | 7/2013 | Vedder |
| 2013/0237892 A1 | 9/2013 | Wardlaw |

OTHER PUBLICATIONS

International Search Report and Written Opinion dated Mar. 14, 2013 for related International Appln. No. PCT/US2012/058387.

* cited by examiner

BRACE FOR CORRECTION OF HUMERAL FRACTURES

CROSS REFERENCE TO RELATED APPLICATION

The present application claims priority under 35 U.S.C. § 119(e) to U.S. Provisional Application Ser. No. 61/542,327, filed on Oct. 3, 2011, the content of which is incorporated herein by reference in its entirety.

BACKGROUND

The present disclosure relates to a device and method for non-surgical correction of humeral fractures.

Approximately 650,000 people suffer a humeral fracture in the United States each year. The distal third fracture of the humerus accounts for approximately 50,000 fractures yearly. Midshaft humeral fractures account for approximately another 200,000 fractures per year.

Many humeral fractures are treated surgically. For example, the large majority of distal third humeral fractures are treated surgically. The cost to surgically repair a humeral fracture ranges from approximately $10,000 to $30,000 per instance. Surgical morbidity is a significant concern, and other surgical risks can add to the cost of treating the fracture.

In contrast, non-surgical treatment is significantly less expensive and involves low or no risk. Distal third and midshaft humeral fractures have been treated non-surgically using known humeral fracture braces, such as a Sarmiento style brace. See Sarmiento A, Kirman P B, Galvin E G, Schmitt R H, Phillips J G, "Functional Bracing of Fractures of the Shaft of the Humerus," *J. Bone Joint Surg.* (*Am*) 1977; 59A; 596-601. However, it is difficult if not impossible to control the distal fragment using known humeral fracture braces. For example, known humeral fracture braces generally do not immobilize the joint above and below the fracture, a protocol often used in the treatment of other fracture types.

Also, humeral fractures often heal with significant angular deformity; the predominant deformity being varus angulation of the distal fragment. In the case of distal third humeral fractures, angular deformity cannot be corrected with existing humeral fracture bracing. In fact, the majority of braces currently available stop short of traversing the distal fragment and leave a long lever arm at the level of the fracture site, which can actually worsen the deformity.

For midshaft humeral fractures, use of known humeral fracture bracing fails to correct angular deformity with some patients. Failure of known methods is particularly common in overweight patients, where the upper arm tends to rest in an abducted rather than neutral position.

As such, there is a need for a device and method for non-surgical treatment of distal third and midshaft humeral fractures that results in reduced angular deformity. Specifically, there is a need for an adjustable rigid orthopedic brace for treatment of humeral fractures, including a means for correcting deformities including varus, valgus, rotational, anterior and/or posterior deformities.

SUMMARY

The present disclosure seeks to solve the above-described needs and other needs by providing an adjustable brace for correcting a humeral bone fracture. A brace according to the present disclosure is secured to a patient's humerus and forearm and uses a hinge arrangement that enables the portion of the brace secured to the patient's forearm to rotate in a plurality of planes relative to the portion of the brace secured to the patient's humerus. Once the brace has been rotated to an appropriate position, the hinge arrangement can be locked so that the brace remains in that position and properly compresses the patient's humeral fracture. The brace allows the patient's arm to be secured in the most advantageous position for the correction of the humeral fracture, to reduce angular deformity and for the comfort of the patient. The hinge arrangement can also be unlocked at any time to allow the brace to be adjusted or to allow the patient to move his or her arm.

The hinge arrangement enables the forearm cuff to move in a plurality of planes relative to the humeral cuff using at least one angular hinge and optionally at least one range of motion hinge. The angular hinge can be used to correct a varus or valgus deformity at the location of a humeral fracture by enabling the forearm cuff to rotate in relation to the humeral cuff in a plane that is different than the natural plane of rotation of the patient's elbow. The range of motion hinge controls flexion and extension of a patient's elbow by enabling the forearm cuff to rotate in relation to the humeral cuff in the natural plane of rotation of the patient's elbow. By utilizing both of these types of hinges, the hinge arrangement enables the forearm cuff to rotate in a plurality of planes in relation to the humeral cuff. These hinges may be locked or unlocked at any time to allow for adjustment of the brace.

The present disclosure further provides a method for treating patients with humeral fractures. A brace according to the present invention may be fit to a patient's arm by locating a humeral cuff on the patient's upper arm and a forearm cuff on the patient's forearm. The patient's forearm may then be rotated into a desired position relative to the patient's upper arm, and the humeral cuff and forearm cuff may be fastened to the respective portions of the patient's arm. Once the patient's arm is in the desired position, the hinge arrangement of the brace may be locked to secure the patient's arm and correct the fracture. The hinge arrangement may then be unlocked whenever the brace needs to be adjusted or the patient needs to move his or her arm.

A brace according to the present disclosure may also be enabled to fit various patients. For example, a brace according to the present disclosure uses various pivot points and length adjustments to suit the needs of the patient. The pivot points and length adjustments not only allow the brace to be adjusted to fit patients with different sized arms, but also to fit patients with fractures at different locations along their arms. In at least one embodiment, the humeral cuff includes separate portions that may be adjusted relative to each other so that they can be positioned to properly compress a humeral fracture regardless of the fracture location. The forearm cuff may be formed in a similarly adjustable manner. The hinge arrangement may also be formed so that the hinges may be positioned at a plurality of locations relative to the patient's arm and the humeral and forearm cuffs.

A brace according to the present disclosure is also enabled to use removable fittings, which allow the brace to be quickly adjusted to suit the needs of differently-sized patients. The present disclosure also allows for the use of various fasteners and straps to adjust the brace and suit the needs of various patients. In at least one embodiment, a shell that is capable of partially, substantially or completely encircling the upper arm of a patient is attached to the humeral cuff and can be adjusted fit the patient's arm. The present disclosure further provides that the brace may be used in connection with a sling or an abduction pillow.

In one embodiment according to the present disclosure, the brace includes a humeral cuff, a forearm cuff, a range of motion hinge, an angular hinge, an upper rigid support and a lower rigid support. According to at least one embodiment of the present disclosure, the angular hinge is connected to the range of motion hinge, the humeral cuff is connected to the angular hinge via the upper rigid support, and the forearm cuff is connected to the range of motion hinge via the lower rigid support. According to at least one embodiment, the humeral cuff includes at least one shell and one or more fasteners. The shell may be formed as a part of the humeral cuff, or may be removably attached to the humeral cuff. The shell may also be configured so that it can be adjusted to different positions with respect to the humeral cuff to custom fit the specific needs of a patient.

It is accordingly one advantage of the present disclosure to provide an orthopedic device that includes a humeral cuff, a forearm cuff, and an angular hinge.

It is another advantage of the present disclosure to provide an orthopedic humeral device that includes a range of motion hinge.

It is a further advantage of the present disclosure to provide an orthopedic humeral device that further includes an upper rigid support and a lower rigid support.

It is yet another advantage of the present disclosure to provide an orthopedic humeral device and a method for treating a distal third humeral fracture via bracing.

Additional features and advantages are described herein, and will be apparent from the following Detailed Description and the figures.

BRIEF DESCRIPTION FOR THE DRAWINGS

The above and other objects, features and advantages of the present disclosure will be apparent from the following detailed description of the preferred embodiments of the disclosure in conjunction with the accompanying drawings, in which.

DETAILED DESCRIPTION

Embodiments of the present disclosure may be understood more readily by reference to the following detailed description. It is to be understood that the terminology used herein is for the purpose of describing particular embodiments only and is not intended to be limiting. Also, as used herein, the singular forms "a," "an" and "the" include plural referents unless the context clearly dictates otherwise.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint.

Figure 1:
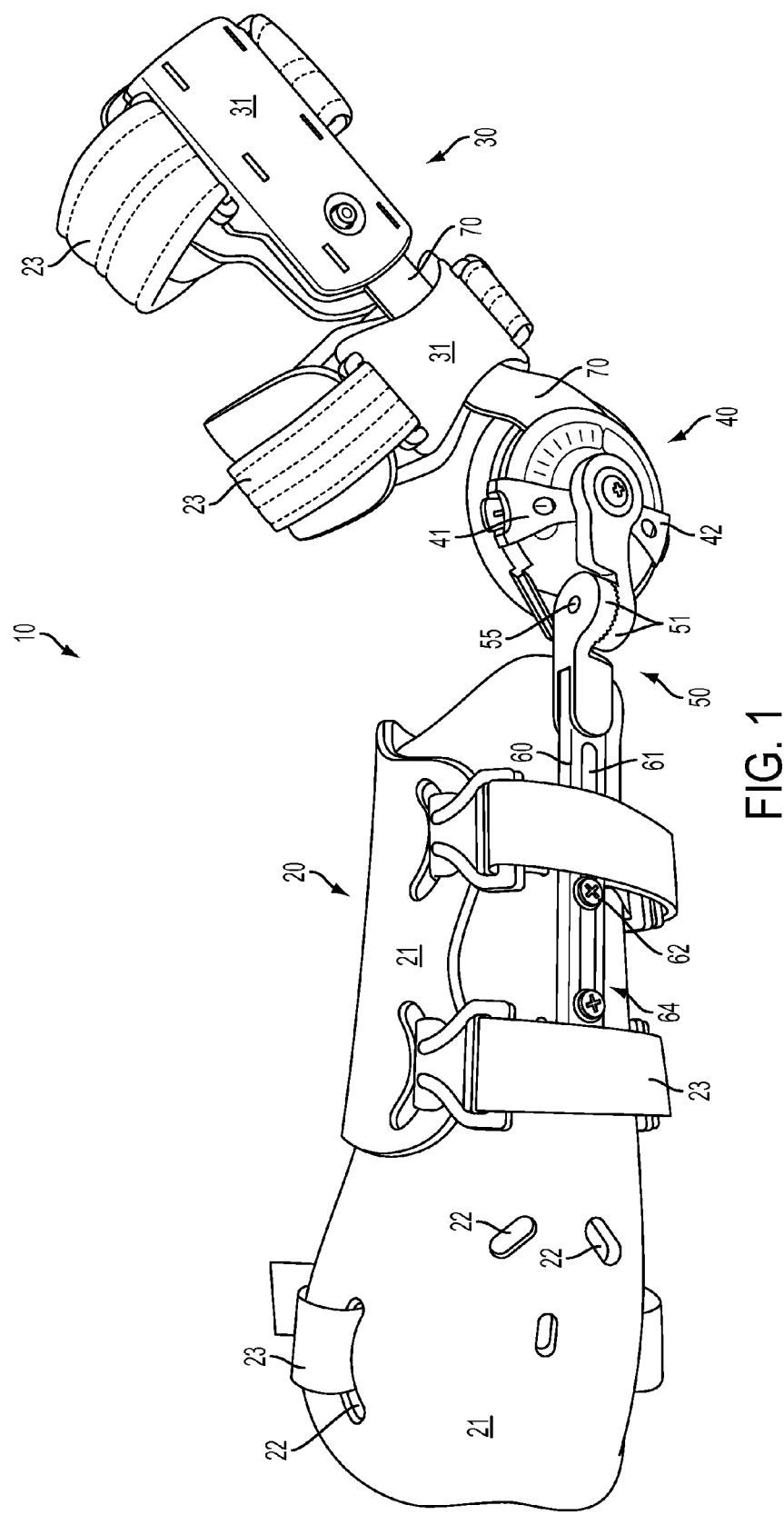
FIG. 1 is a perspective view showing a device in accordance with an embodiment of the disclosure.

Referring to FIG. 1, an exemplary device 10 having a humeral cuff 20, a forearm cuff 30, a range of motion hinge 40, an angular hinge 50, an upper rigid support 60 and a lower rigid support 70 in accordance with an embodiment of the present disclosure is shown. According to at least one embodiment of the present disclosure, as shown in FIG. 1, the angular hinge 50 is connected to the range of motion hinge 40, the humeral cuff 20 is connected to the angular hinge 50 by the upper rigid support 60, and the forearm cuff 30 is connected to the range of motion hinge 40 by the lower rigid support 70 such that the forearm cuff 30, the range of motion hinge 40, the angular hinge 50 and the humeral cuff 20 are connectively positioned in series along the length of the device 10 with the forearm cuff 30 more proximal to the range of motion hinge 40 than the angular hinge 50 and the humeral cuff 20 more proximal to the angular hinge 50 than the range of motion hinge 40.

Figure 5:
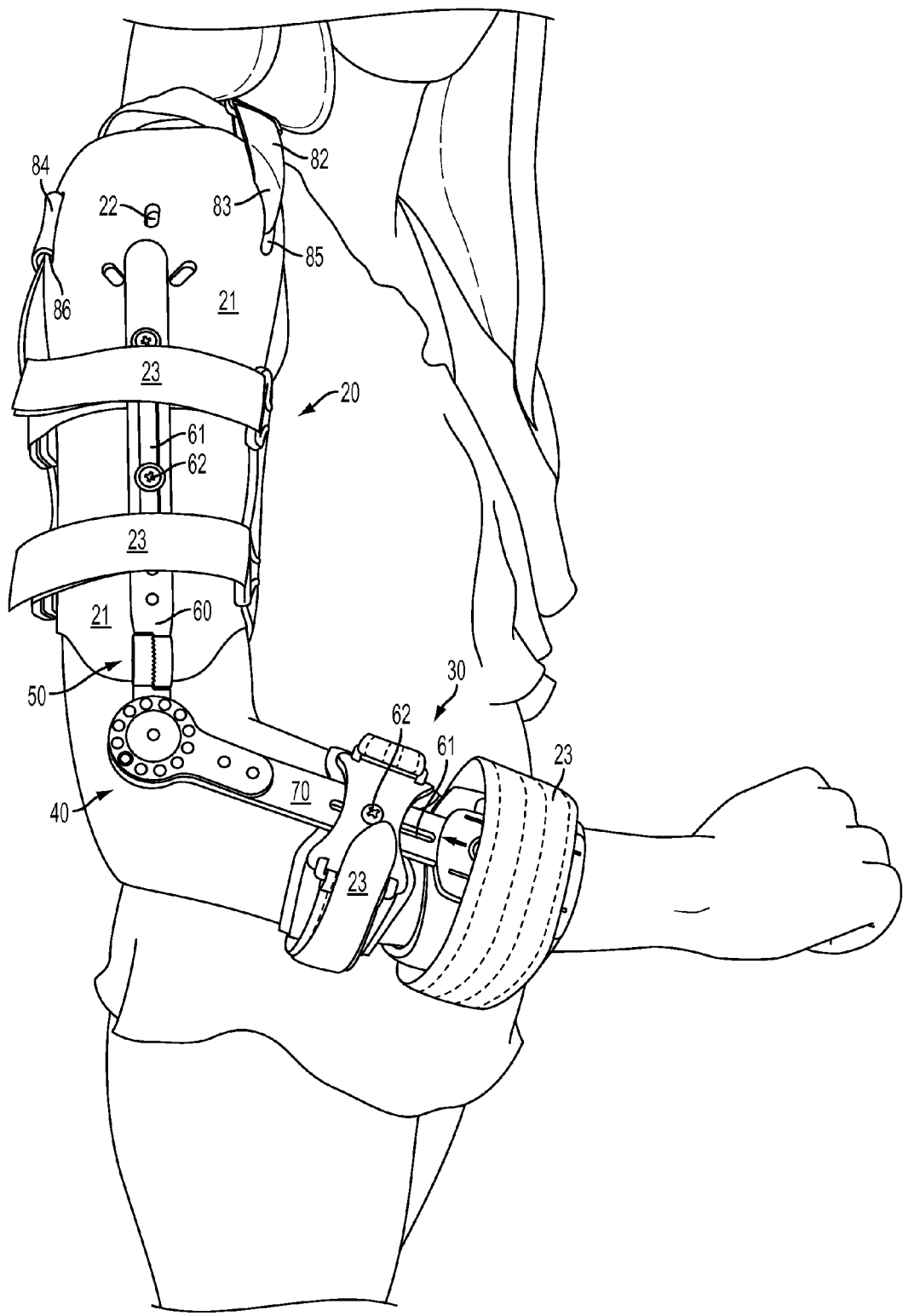
FIG. 5 is a right side view showing a device in accordance with an embodiment of the disclosure, as applied to a patient.

The humeral cuff 20 may be any cuff capable of being secured to an upper or humeral arm portion of a patient and applying compression to at least the proximal fracture fragment. Humeral cuff 20 may take various forms. According to at least one embodiment, as shown in FIG. 1, the humeral cuff 20 includes at least one shell 21 and one or more fasteners 23. The humeral cuff 20 may be a lateral cuff (as shown in FIGS. 1 and 5), a medial cuff (not shown), an anterior cuff (not shown), or have other suitable forms. The humeral cuff 20 may be any length necessary to cover the desired portion of the patient's arm.

Figure 6:
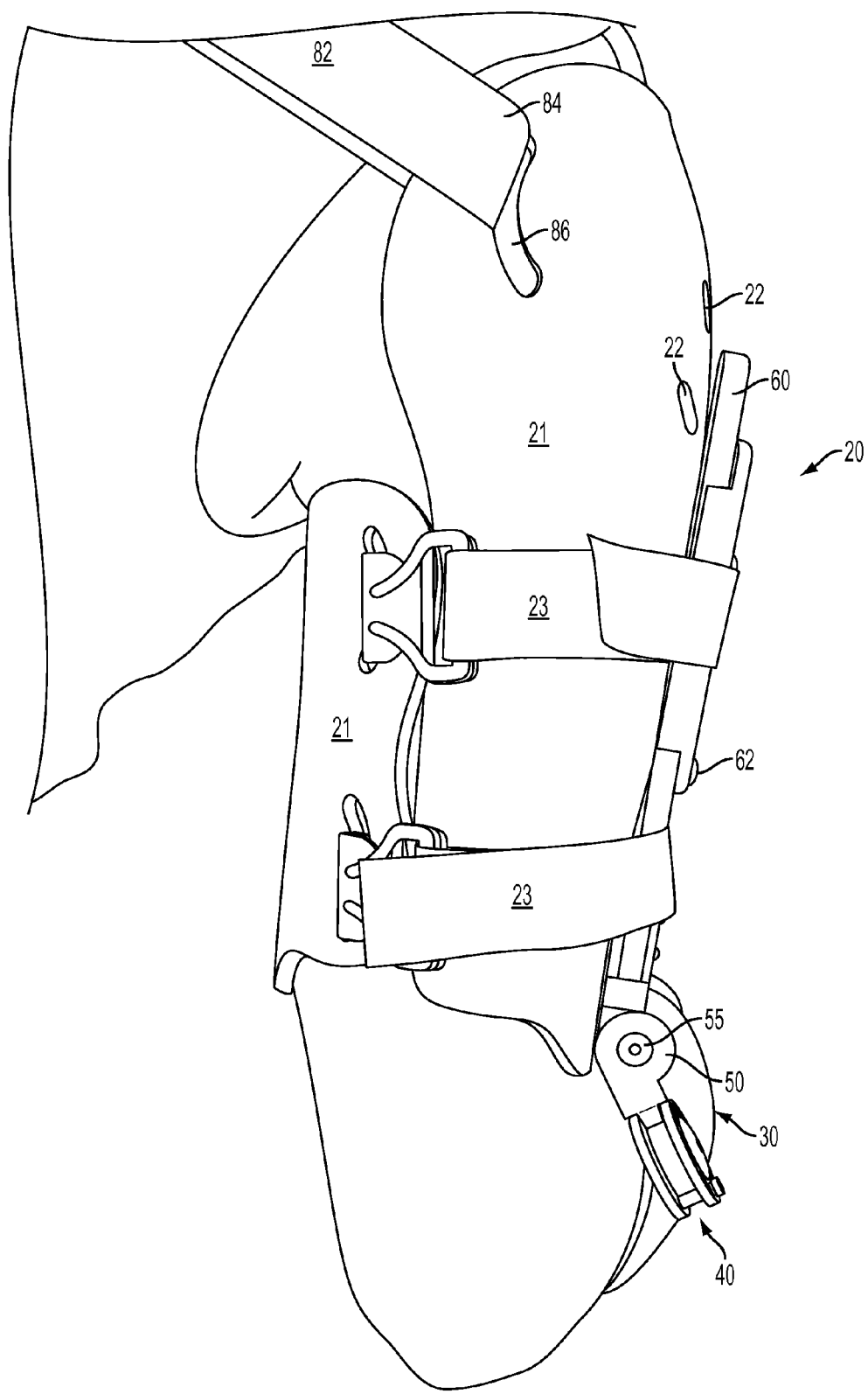
FIG. 6 is a rear view showing a device in accordance with an embodiment of the disclosure, as applied to a patient.

In the illustrated embodiment, an upper portion of humeral cuff 20 which is contoured as shown in FIGS. 5 and 6, covers a lateral portion of a patient's shoulder via outer shell 21 only, while the lower portion of cuff 20 covers a lateral portion of the patient's lower humerus, near the patient's elbow, via inner and outer shells 21. However, the humeral cuff 20 may be designed to cover any desired length or portion of the patient's upper arm and may be positioned to cover any desired length or portion of the patient's upper arm. For example, the humeral cuff 20 may be designed to extend from (i) the lateral neck of the patient to the lateral elbow condyle of a patient, (ii) from the axilla to the medial epicondyle of the patient, or (iii) from the acromioclavicular joint to the anticubital fossa of the patient.

The humeral cuff 20 may also be provided with separate segments that allow the length of the cuff to be adjusted to fit a patient's arm. For example, the upper (at apertures 22) and lower (at upper support 60) portions of the humeral cuff 20 may be separate segments and telescope into each other or fold over each other. The upper and lower portions of humeral cuff 20 may also be adjustable relative to each other via a slotted track, sliding bar and screw, similar to upper rigid support 60 described below, or by another adjustment design known in the art.

It is advantageous for the lower portion of the humeral cuff 20, which covers a lateral portion of the humerus in the illustrated embodiment, to be adjustable so that the lower portion can be positioned to properly compress a humeral fracture regardless of the fracture location. If the device 10 includes a medial cuff or an anterior cuff, as suggested above, it is also advantageous for those cuffs to be similarly adjustable along a patient's arm to also be positioned to properly compress a humeral fracture.

Further alternatively, the lower portion (at upper support 60) of humeral cuff 20 may be designed to rotate around a patient's arm so as to be positioned in a desired lateral, medial or anterior area of the patient's arm to properly compress a humeral fracture. If humeral cuff 20 is adjustable, it is important that the cuff be stable on the patient's arm to maintain desired positioning and to compress a humeral fracture properly. The stabilization of cuff 20 can be accomplished, for example, by providing additional fasteners 23 on the humeral cuff 20 and/or by providing a shoulder strap 82 as described below in connection with FIGS. 5, 6, 7A and 7B.

In another alternative embodiment, the humeral cuff 20 may be designed with removable fittings to allow device 10 to fit different patients. For example, different humeral cuffs 20 taking into account differing arm sizes and differing fracture locations could be removably attachable to device 10, so that the proper cuff can be substituted into device 10 based on the relevant characteristics of the patient. Different portions of the humeral cuff 20 may also be removably attached to each cuff, e.g., via hook and loop fasteners, so that device 10 may better fit different patients. The forearm cuff 30 described below may also be designed with removable fittings to allow the device to custom fit differently sized patients.

According to at least one embodiment, shell 21 is a shell 21 capable of partially, substantially, or fully encircling the upper arm of a patient. In the illustrated embodiment, shell 21 includes two or more shells 21, which used in combination are capable of partially, substantially, or fully encircling the upper arm of a patient. The shell 21 may be of plastic, metal, carbon fiber, composite, and/or any other rigid or substantially rigid material sufficient to hold compression on the upper arm of a patient. The shell material includes but is not limited to, carbon fiber, polyethylene, polypropylene, graphite, copolymer, KEVLAR®, DELRIN®, KYDEX®, lamination, aluminum, titanium, tungsten and/or steel, magnesium or any combination thereof. Shell 21 can be made of a material having a radiolucent character. In some embodiments, the shell 21 includes apertures 22 for purposes including, but not limited to, increased air flow to the skin, reduced weight, reduced cost, and/or for securing a fastener 23. The shell 21 may be formed as a part of humeral cuff 20, or may be removably attached to humeral cuff 20. The shell 21 may also be designed so that it can be adjusted to different positions with respect to humeral cuff 20 to best suit the specific needs of a patient.

Figure 2:
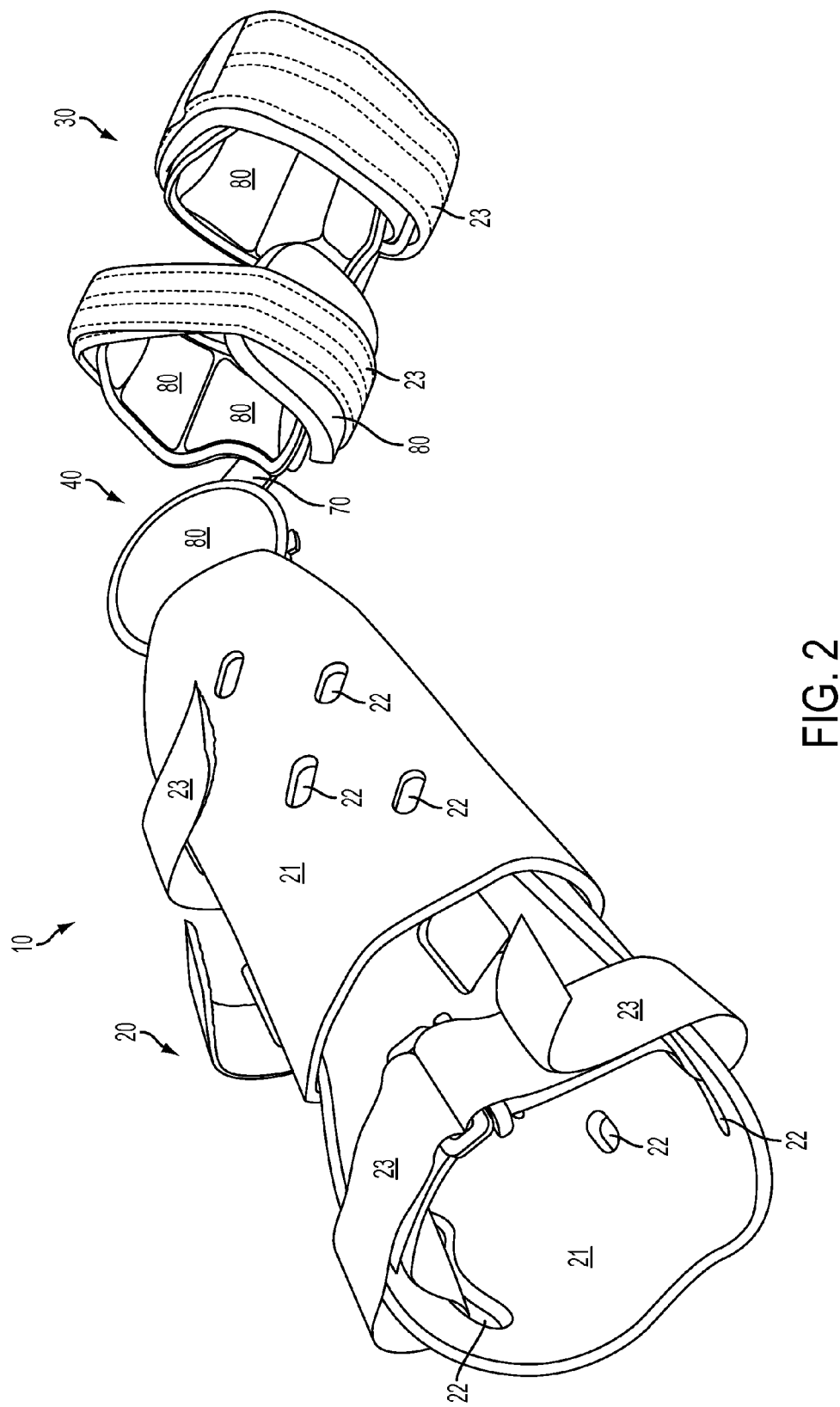
FIG. 2 is another perspective view showing a device in accordance with an embodiment of the disclosure.

The one or more fasteners 23 are used to secure the shell 21 around the patient's arm. The fasteners 23 may be any type or design sufficient to fasten the shell 21 around the arm of the patient in a manner that provides sufficient compression. The fasteners 23 may be expandable, adjustable and/or otherwise configured to accommodate upper arms of various sizes and shapes. According to at least one embodiment, as shown in FIGS. 1 and 2, the fasteners 23 include closure straps integrally provided with hook and loop fasteners to enable release of the closure strap or adjustment of the length of the closure strap such that the shell 21 is securely affixed to the patient's arm. Alternatively, the fasteners 23 may include or form buckles, clamps, laces, latches, ratchets, elastic closures, snaps, hooks, buttons, zippers and/or friction-based fasteners.

According to an alternative embodiment (not shown), the humeral cuff 20 includes a support piece 31 operating with one or more fastener 23. The support piece 31 (similar to piece 31 illustrated in FIG. 1 for forearm cuff 30) may be rigid and/or flexible and may have any shape or size necessary for placement against some portion of the upper arm of a patient. The one or more fasteners 23 may be used to secure the support piece 31 against the upper arm of a patient.

As illustrated in FIG. 1, brace 10 further includes a forearm cuff 30. Forearm cuff 30 provides a device for securing brace 10 to the forearm of a patient, and may take various forms. According to the illustrated embodiment, forearm cuff 30 includes one or more fasteners 23 (including all alternatives for fasteners 23 discussed above) for securing brace 10 to the patient's forearm. In the illustrated embodiment, forearm cuff 30 includes a plurality of support pieces 31, each having one or more fasteners 23. Support pieces 31 may be rigid or flexible and may be any shape or size necessary for placement against some portion of the forearm of a patient. Support pieces 31 may be made of any of the materials discussed above for shells 21. Support pieces 31 may be fixedly attached or moveably attached, e.g., slidably attached, to rigid lower support. Shells 21 and/or support pieces 31 can each have inner foam, padded, or otherwise soft liners for patient comfort.

As shown in FIG. 1, the fasteners 23 of forearm cuff 30 can include closure straps integrally provided with hook and loop fasteners to enable release of the closure strap or adjustment of the length of the closure strap such that brace 10 can be securely affixed to the patient's forearm. Alternatively, the fasteners 23 may include buckles, clamps, laces, latches, ratchets, elastic closures, snaps, hooks, buttons, zippers and/or friction-based fasteners.

According to yet other embodiments (not shown), the forearm cuff 30 includes at least one shell (like shells 21) capable of partially, substantially or fully encircling the forearm of a patient. One or more fasteners 23 is used to secure the one or more forearm shells as has been described with respect to humeral cuff 20.

The range of motion hinge 40 may be of any rigid or substantially rigid material, including, but not limited to, carbon fiber, polyethylene, polypropylene, graphite, copolymer, KEVLAR®, DELRIN®, KYDEX®, lamination, aluminum, titanium, tungsten and/or steel, or any combination thereof. The range of motion hinge 40 is made of radiolucent material in one embodiment.

Figure 3:
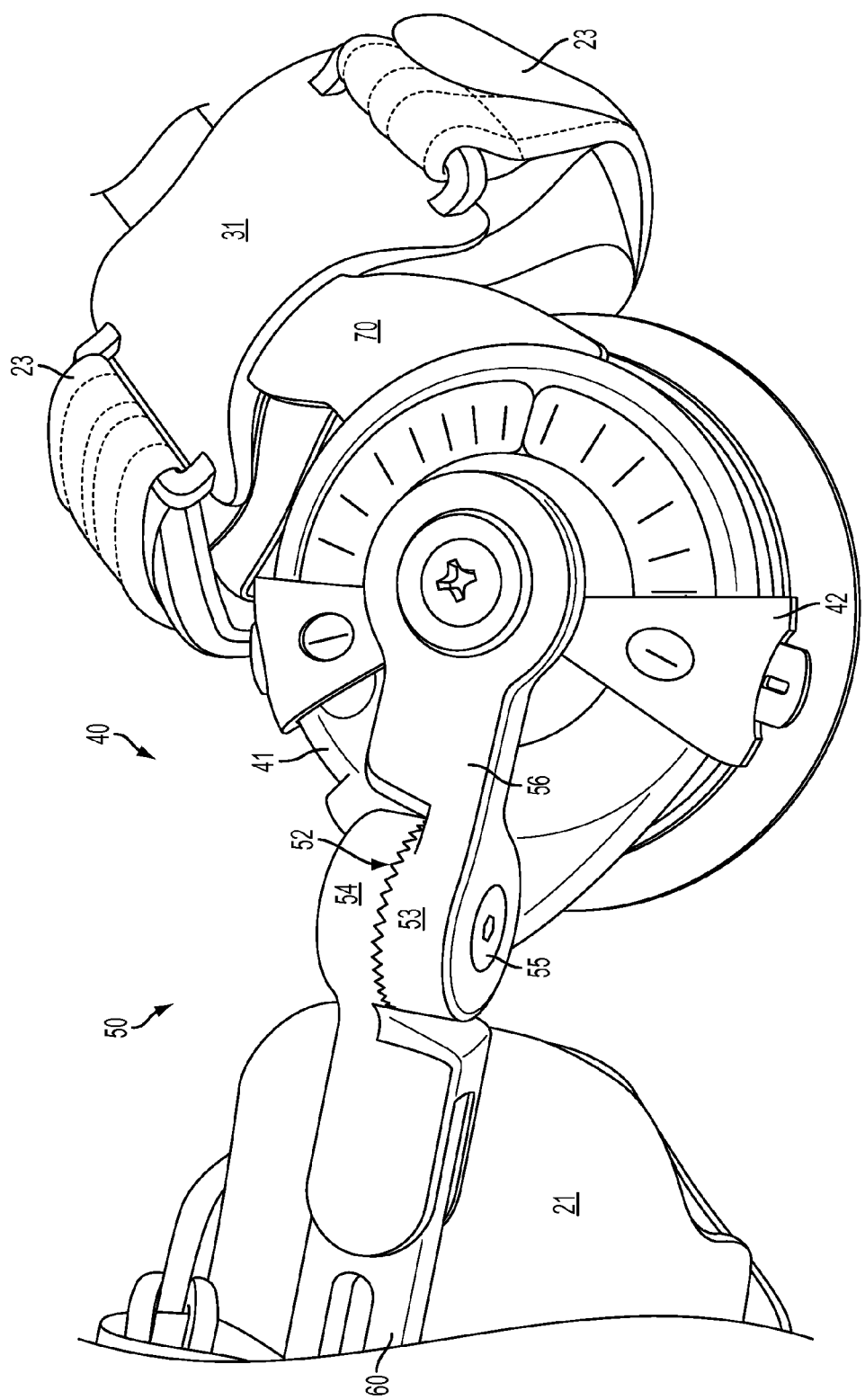
FIG. 3 is an exploded perspective view showing a range of motion hinge and an angular hinge in accordance with an embodiment of the disclosure.

The range of motion hinge 40 controls flexion and extension of a patient's elbow. According to at least one embodiment, range of motion hinge 40 pivotally connects the humeral cuff 20 to the forearm cuff 30 and enables rotation of the humeral cuff 20 and/or forearm cuff 30 about a set range of motion provided by hinge 40. According to at least one embodiment, and as shown in FIG. 3, the range of motion hinge 40 is a releasably locking rotation hinge with adjustable rotation limits. The releasably locking rotation hinge includes a flexion rotation stop 41 and an extension rotation stop 42. When locked, the range of motion hinge 40 is maintained in a static position. When unlocked, the range of motion hinge 40 permits a specific range of elbow motion as determined by the setting of the flexion rotation stop 41 and the extension rotation stop 42. Notwithstanding the foregoing, the range of motion hinge 40 is not limited to any one specific construction or type of hinge. By way of example, the range of motion hinge 40 may include a hinge mechanism, including, but not limited to, push pins, ratchets, teeth, locked pegs, discs or dials, clutch joints, ball and socket joints, dynamic joints, locking spring joints, screws, overlap joints, and/or polycentric joints with removable locks. One suitable range of motion hinge 40 provided by the assignee of the present disclosure is the Bledsoe T-Chek elbow brace.

According to at least one embodiment, the range of motion hinge 40 is adjustable from about −20 to about 150 degrees of motion, with zero degrees representing a fully extended arm. According to other embodiments, the range of motion hinge 40 may be a static joint, which does not permit rotation of forearm cuff 30 relative to humeral cuff 20 about the range of motion hinge 40, in which case brace 10 functions as a splint. Or, an adjustable version of hinge 40 can be locked place or made to have a zero degree range of rotation, in which case brace 10 likewise functions as a splint.

The brace 10 further includes the angular hinge 50 located above the range of motion hinge 40. Angular hinge 50 can likewise be made of any rigid or substantially rigid material, including, but not limited to, carbon fiber, polyethylene, polypropylene, graphite, copolymer, KEVLAR®, DELRIN®, KYDEX®, lamination, aluminum, titanium, tungsten and/or steel, or any combination thereof. The angular hinge 50 can also be made of a radiolucent material.

Angular hinge 50 is adjusted as necessary to correct a varus or valgus deformity at the location of the fracture. The angular hinge 50 includes one or more hinge components 51, a hinge interface 52 (FIG. 3) and an adjuster 55. The angular hinge 50 is in one embodiment capable of adjustment from about −30 to about 60 degrees of varus and/or valgus angulation with zero degrees having no angulation and being within the same plane as the range of motion hinge 40.

Figure 4:
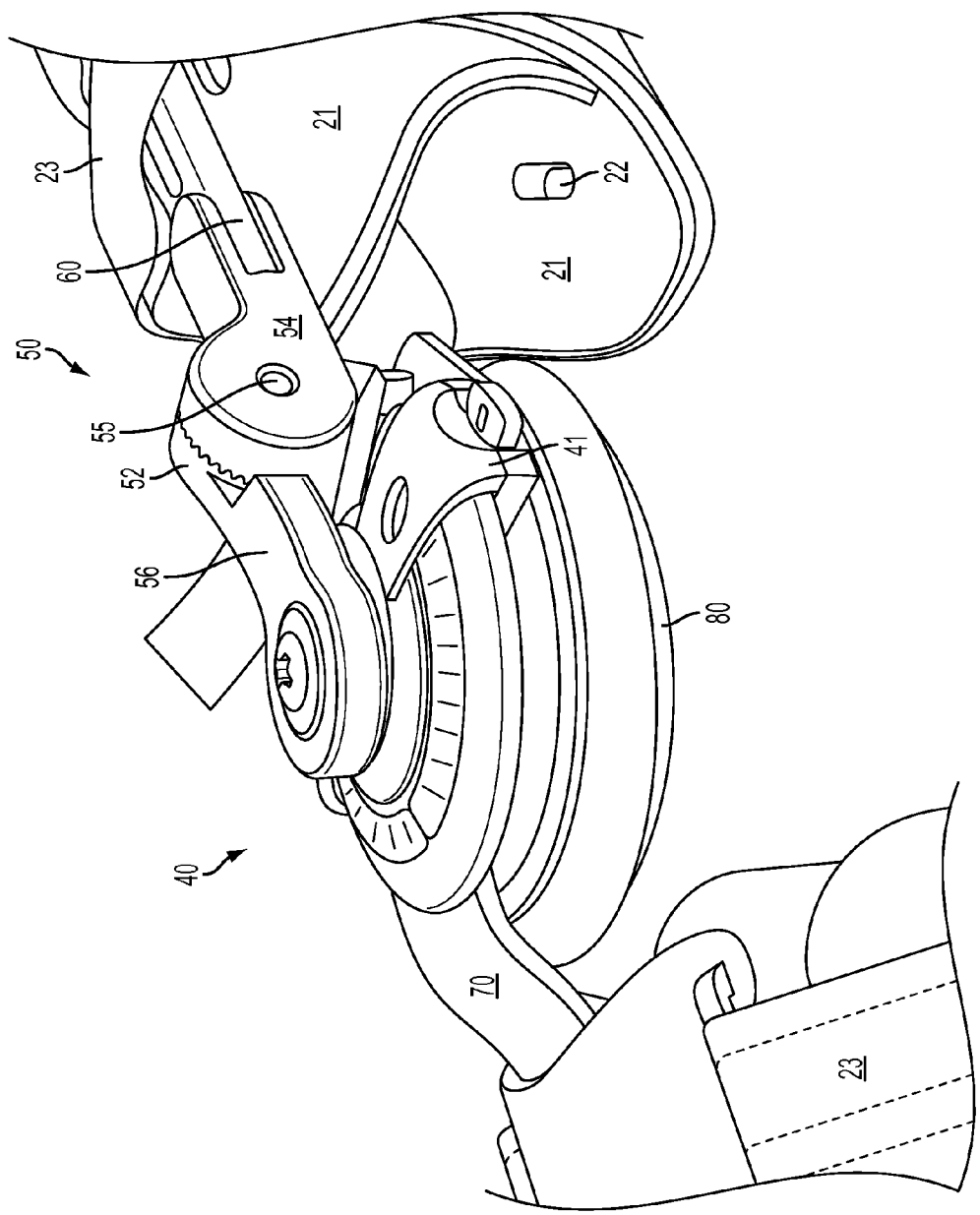
FIG. 4 is another exploded perspective view showing the range of motion hinge and the angular hinge in accordance with an embodiment of the disclosure.

According to at least one embodiment, as shown in FIGS. 3 and 4, the hinge components 51 of FIG. 1 include a first hinge portion 53 and a second hinge portion 54. According to the embodiment shown in FIG. 3, the hinge interface 52 includes each portion 53 and 54 having mating teeth, wherein each tooth represents an angular adjustment of approximately eight degrees. In other embodiments, each tooth represents an angular adjustment of a different number of degrees, for example, ranging from about one degree per tooth to about twenty degrees per tooth. According to yet other embodiments, the one or more hinge portions 53 and 54 include toothless or smooth surfaces, which removably lock together by interference fit (also referred to as a press fit or friction fit) and are slidably adjustable with respect to each other. According to still other embodiments, hinge interface 52 includes one or more push pins, ratchets, locked pegs, discs or dials, clutch joints, ball and socket joints, dynamic extension/flexion joints, locking spring joints, screws, overlap joints, and/or polycentric joints with removable locks.

In the illustrated embodiment of FIG. 3, adjuster 55 includes a bolt or screw with a hexagonal socket configured to receive a mated tool with a hexagonal cross-section. Adjusting bolt 55 is inserted into hinge portion 53 and threaded into hinge portion 54. Adjusting bolt 55 alternatively has a wing nut or other tab for manually loosening and tightening. Hinge portions 53 and 54 can alternatively both include through holes, which receive adjusting bolt 55, which in turn receives a mating nut for loosening and tightening.

As illustrated in FIGS. 3 and 4, range of motion hinge 40 is connected to the angular hinge 50 by an arm 56. In the illustrated embodiment, arm 56 is formed with and extends from hinge portion 30 to the center of range of motion hinge 40. Arm 56 thereby sets the distance between the centers of hinges 40 and 50. In the illustrated embodiment of FIGS. 3 and 4, an axis through the center of hinge 40 is at least substantially orthogonal to the center of hinge 50.

Arm 56 is secured to range of motion hinge 40 by a suitable means, including but not limited to rivets, welding, threaded fastening and/or friction fit. According to other embodiments, and as shown in FIG. 6, arm 56 and one or more components of range of motion hinge 40 may be a continuous piece of manufacture. Arm 56 may be provided in various lengths, resulting in a varying distance between range of motion hinge 40 and angular hinge 50, to account for humeral fractures at different positions along the humeral shaft. Arm 56 may also be formed so that the length of arm 56 is adjustable between the centers of range of motion hinge 40 and angular hinge 50 to accommodate patients of various sizes. For example, arm 56 may instead be two slidingly engaging pieces, one of which is slotted, the other of which is threaded to allow the two pieces of arm 56 to be adjustably fixed at different positions relative to each other.

According to at least one embodiment, and as shown in FIGS. 5 and 6, brace 10 may be configured such that range of motion hinge 40 and the angular hinge 50 are oriented laterally with respect to the patient's arm, that is, located on the outside of the patient's arm. According to another embodiment, range of motion hinge 40 and angular hinge 50 are instead oriented medially with respect to the arm of the patient, that is, located on the inside of the patient's arm. According to yet another embodiment, the brace 10 may consist of two range of motion hinges 40 and/or two angular hinges 50 positioned on both the medial and lateral sides of the brace 10.

Further alternatively, more than one range of motion hinge 40 or angular hinge 50 may be used on the same side of the brace 10 to allow for adjustment at multiple predetermined locations. According to yet another embodiment, angular hinge 50 may be adjustable relative to range of motion hinge 40 and/or upper rigid support 60. For example, a slotted track, sliding bar and screws and/or an additional hinge may connect angular hinge 50 to range of motion hinge 40 and/or upper rigid support 60, so that angular hinge 50 may be positioned at a plurality of locations relative to range of motion hinge 40 or upper rigid support 60.

Hinge portions 53 and 54, arm 56 and upper rigid support 60 can be made of a rigid or substantially rigid material, including, but not limited to, carbon fiber, polyethylene, polypropylene, graphite, copolymer, KEVLAR®, DELRIN®, KYDEX®, lamination, aluminum, titanium, tungsten and/or steel, or any combination thereof. Hinge portions 53 and 54, arm 56 and upper rigid support 60 can be made of a radiolucent material. Upper rigid support 60 is connected to the angular hinge 50 by any suitable means, including, but not limited to rivets, welding, and friction fit. Alternatively, upper rigid support 60 and at least one portion of the angular hinge 50 are one continuous piece of manufacture.

Figure 7A:
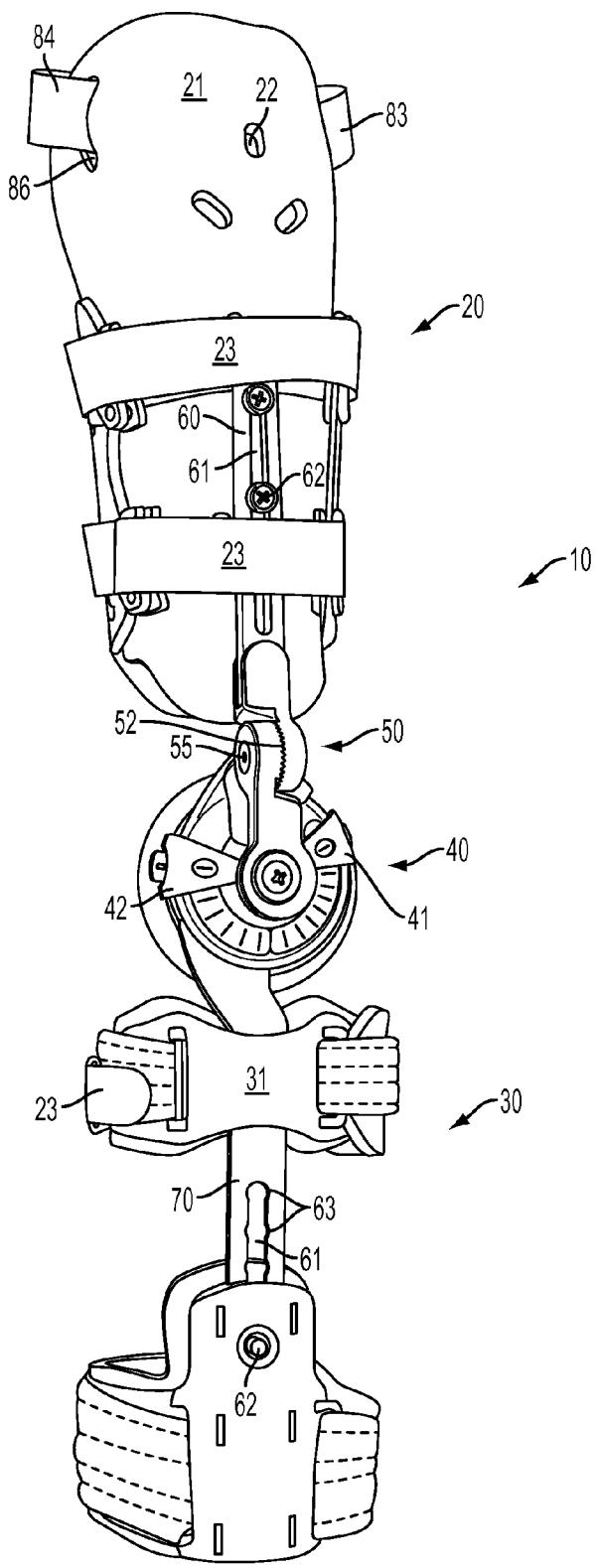
FIG. 7A is a right side view showing the device in accordance with an embodiment of the disclosure.
Figure 7B:
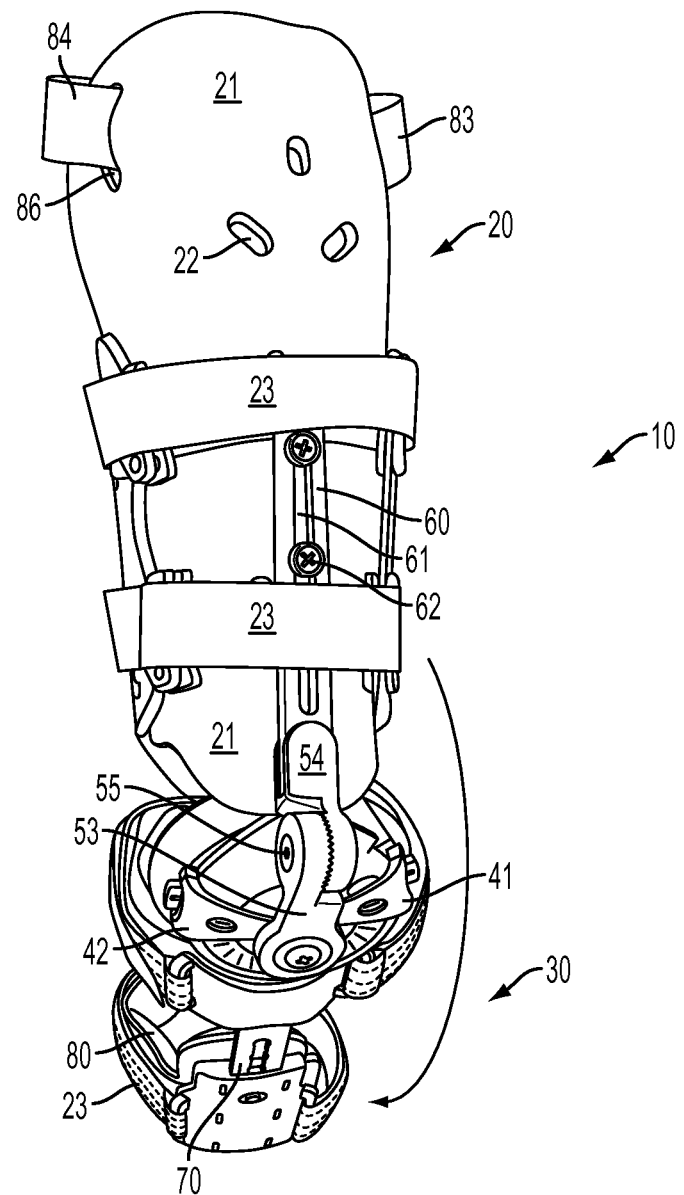
FIG. 7B is a right side view of the device of FIG. 7A showing adjustment of the angular hinge in a varus or inward direction in accordance with an embodiment of the present disclosure.
Figure 8A:
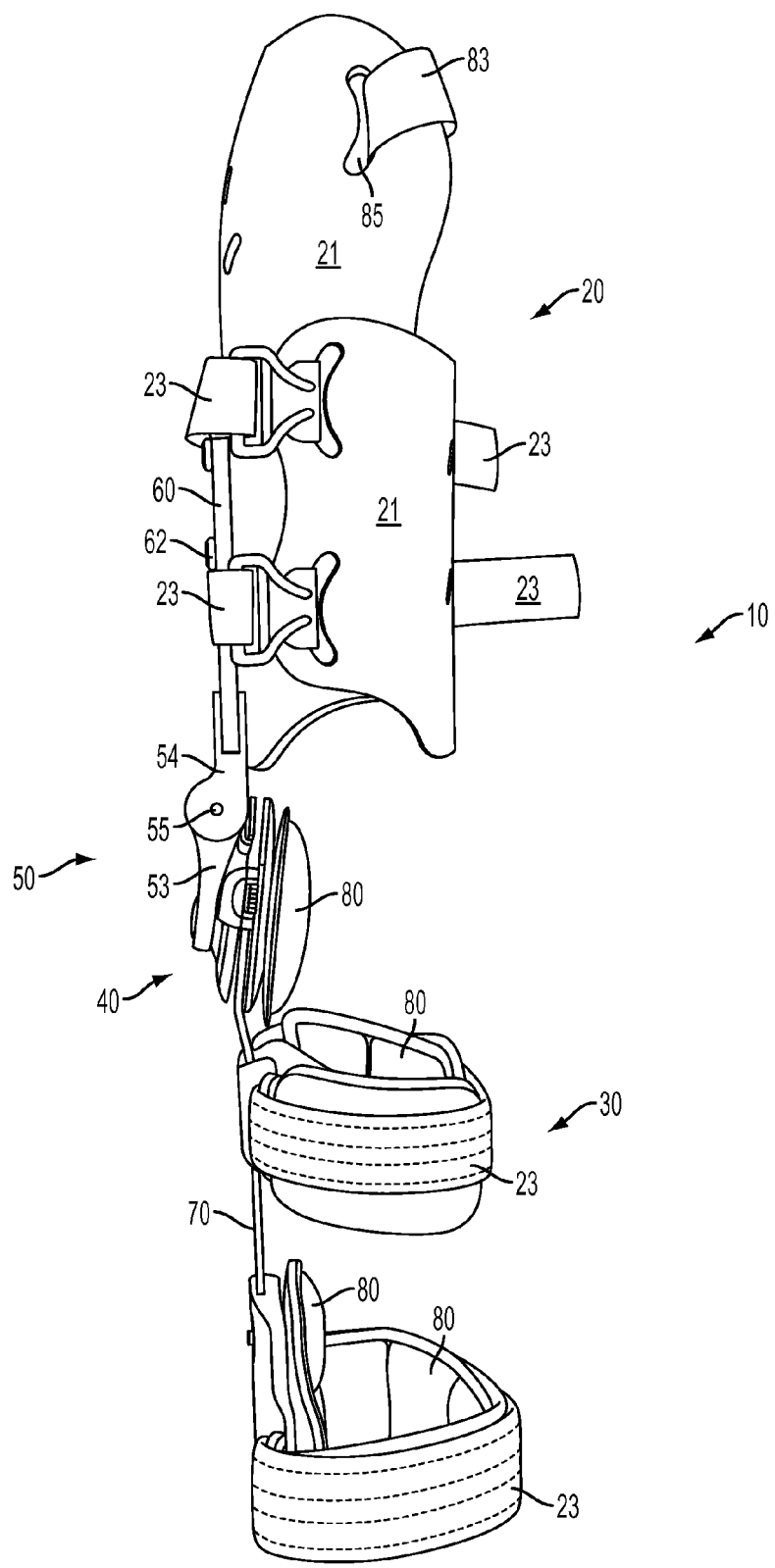
FIG. 8A is a front view of the device in accordance with an embodiment of the present disclosure.
Figure 8B:
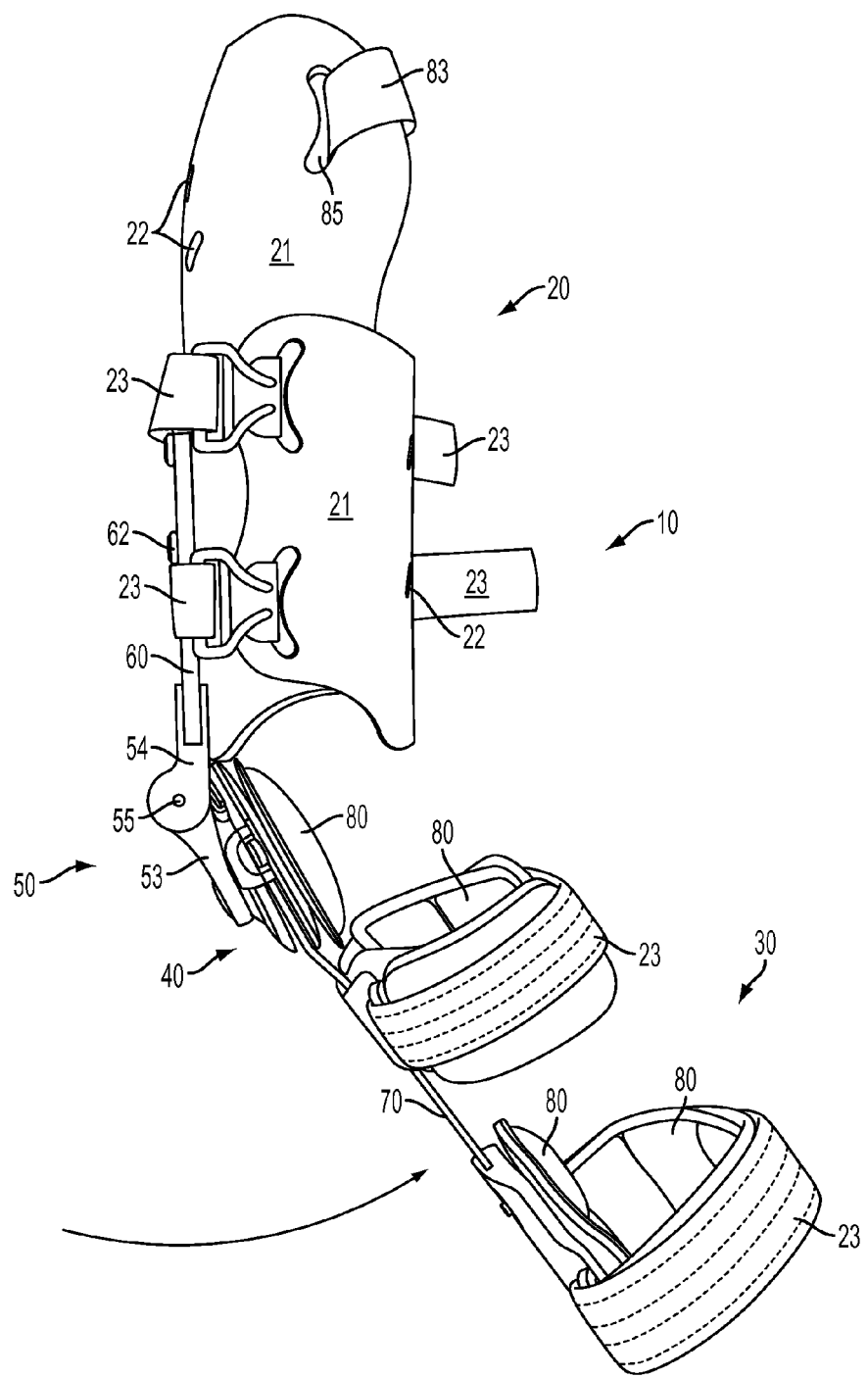
FIG. 8B is a front view of the device of FIG. 8A showing adjustment of the angular hinge in a varus or inward direction.

According to at least one embodiment, and as shown in FIG. 1, upper rigid support 60 connects the humeral cuff 20 to the angular hinge 50. The upper rigid support 60 preferably includes adjustment apparatus 64 for adjusting the distance between the humeral cuff 20 and the angular hinge 50. However, a non-adjustable upper rigid support 60 is also within the scope of the present disclosure. As shown in FIG. 7A, and by way of example only, the upper rigid support 60 in one embodiment includes a substantially vertical channel 61 for accepting screws or other fasteners 62 used to secure upper rigid support 60 to the humeral cuff 20. Vertical channel 61 may be of uniform width to allow for infinite adjustment of the humeral cuff 20 with respect to the upper rigid support 60. Alternatively, the vertical channel 61 may include areas of increased width 63 to allow for incremental or setting adjustment of the humeral cuff 20 with respect to the upper rigid support 60.

In other examples, adjustment apparatus 64 includes a sliding mechanism for adjusting the distance between the humeral cuff 20 and the angular hinge 50. In still other embodiments, the humeral cuff 20 may include a horizontally positioned rotational fixation bar, a horizontal channel, a series of horizontally positioned openings for receiving the screw 62, or any other means of rotational fixation, to allow rotation of the humeral cuff 20 with respect to the upper rigid support 60, in a manner that accommodates or causes internal or external rotation of the patient's upper arm. According to yet other embodiments, upper rigid support 60 and the humeral cuff 20 are one continuous piece of manufacture.

Upper rigid support 60 may further alternatively be pivotally connected to humeral cuff 20 using a screw, cam, wedge, or other method known in the art so that humeral cuff 20 can rotate about the patient's arm in relation upper rigid support 60 and be positioned to best compress a fracture. If humeral cuff 20 is enabled to rotate in relation to rigid support 60, the pivoted connection is able to be locked to lock humeral cuff 20 into a position once an ideal compression position is achieved.

According to at least one embodiment, and as shown in FIG. 7A, lower rigid support 70 connects forearm cuff 30 to range of motion hinge 40. The lower rigid support 70 can include adjustment apparatus 62 for adjusting the distance between the forearm cuff 30 and the range of motion hinge 40. However, a non-adjustable lower rigid support 70 is also within the scope of the present disclosure. As shown in FIG. 7A, and by way of example only, lower rigid support 70 includes a channel 61 for accepting screws 62 used to secure the lower rigid support 60 to forearm cuff 30. Channel 61 may be of uniform width to allow for infinite adjustment of the forearm cuff 30 with respect to the lower rigid support 70. Alternatively, the channel 61 may include areas of increased width 63 to allow for incremental adjustment of the forearm cuff 30 with respect to the lower rigid support 70. In other examples, adjustment apparatus 62 includes a sliding mechanism for adjusting the distance between the forearm cuff 30 and the range of motion hinge 40. In still other embodiments, forearm cuff 30 may include a horizontally positioned rotational fixation bar, a horizontal channel, a series of horizontally positioned openings for receiving the adjustment apparatus or screw 62, or any other apparatus for rotational fixation, which allows rotation of the forearm cuff 30 with respect to the lower rigid support 70 in a manner that accommodates pronation and/or supination of the patient's forearm.

According to yet other embodiments, lower rigid support 70 and forearm cuff 30 are one continuous piece of manufacture. The lower rigid support 70 may be made of any rigid or substantially rigid material, including, but not limited to, carbon fiber, polyethylene, polypropylene, graphite, copolymer, KEVLAR®, DELRIN® KYDEX®, lamination, aluminum, titanium, magnesium, tungsten and/or steel, or any combination thereof. The lower rigid support 70 is made of a radiolucent material in one embodiment. Lower rigid support 70 is connected to the range of motion hinge 40 by a suitable apparatus, including, but not limited to rivets, welding, threaded fasteners, and/or friction fit. Alternatively, the lower rigid support 70 and at least one portion of the range of motion hinge 40 are one continuous piece of manufacture.

According to other embodiments of brace 10, the brace includes the humeral cuff 20, the forearm cuff 30, the range of motion hinge 40 and the angular hinge 50. According to these embodiments, one of the one or more hinge components 51 (portions 53 and 54 (FIG. 3)) is secured directly to the humeral cuff 20 by a suitable structure, including but not limited to rivets, threaded engagement, welding and/or friction fit. Alternatively, one of the one or more hinge components 51 and the humeral cuff 20 are a continuous piece of manufacture. Likewise, a portion of the range of motion hinge 40 may be secured directly to the forearm cuff 30 by any suitable structure, including but not limited to rivets, welding, threaded connection, and/or friction fit. Alternatively, a portion of the range of motion hinge 40 and the forearm cuff 30 may be a continuous piece of manufacture.

According to yet other embodiments of the brace 10, the brace 10 includes the humeral cuff 20, the forearm cuff 30 and the angular hinge 50, but not the range of motion hinge 40. According to these embodiments, one of the one or more hinge components 51 (portions 53 and 54 (FIG. 3)) is secured directly to the humeral cuff 20 by any suitable means, including but not limited to rivets, welding, threaded fastening, and/or friction fit. Alternatively, the upper rigid support 60 may connect the humeral cuff 20 to the angular hinge 50 as described above. As a further alternative, one of the one or more hinge components 51 and the humeral cuff 20 are a continuous piece of manufacture. Likewise, one of the one or more hinge components 51, and any extension thereof, may be secured directly to the forearm cuff 30 by any suitable means, including but not limited to rivets, welding, threaded fastening, and/or friction fit. Alternatively, the lower rigid support 70 may connect the forearm cuff 30 to at least one portion of the angular hinge 50. As a further alternative, one of the one or more hinge components 51 and the forearm cuff 30 may be a continuous piece of manufacture.

According to at least one embodiment, and as shown in FIG. 2, the brace 10 includes one or more cushions 80 configured to decrease friction between the brace 10 and the patient and to enhance comfort. It is advantageous for the cushions 80 to be positioned within humeral cuff 20 in an area near the humeral fracture to correct the alignment of the bone and for patient comfort. Cushions 80 may be of a type known in the art, including, but not limited to, foam pads, gel pads, and/or air, liquid or gel-filled bladders. The cushions 80 may be porous or non-porous, perforated or non-perforated, sectional or non-sectional. Cushions 80 may include any suitable surface material, including, but not limited to, any known fabric such as cotton, wool or GORE-TEX®. According to at least one embodiment, the cushion surface material includes a micro-ridged structure to prevent the growth of bacteria. Cushions 80 may also be waterproof, so that an antibacterial or antimicrobial agent or gel can be applied to the patient's arm without seeping into the cushion upon contact. The cushions 80 may be permanently or removably fixed to device or brace 10 by a suitable means, including but not limited to an adhesive, a hook and loop fastener, and/or via threaded fastening.

According to other embodiments, device 10 may further include a wrist and hand extension (not shown) extending distally from the forearm cuff 30 and contoured to fit the patient's palm. The extension may be secured to the forearm cuff 30 by a suitable means, such as via hook and loop straps 23. According to one embodiment, and by way of example only, the support piece 31 of forearm cuff 30 is configured to receive the extension and permanently or removably and adjustably secure the extension to the forearm cuff 30.

Device or brace 10 may also be provided so as to be specific to a patient's right arm or left arm. Alternatively, brace 10 may be provided in a single embodiment that is capable of serving as a right arm brace or a left arm brace. Further, brace 10 and each of its components may be provided in various sizes to accommodate a variety of patients. By way of example only, brace 10 can be provided in sizes including adult extra small, adult small, adult medium, adult large, and adult extra large. Brace 10 can also be provided in one or more pediatric sizes and one or more bariatric sizes. Alternatively, brace 10 may be provided in one size (or a couple of sizes) that is (are) capable of accommodating patients of many or all sizes.

According to at least one embodiment, brace 10 further includes a support strap 82 for securing the brace 10 to the upper torso of a patient. Specifically, support strap 82 is configured to prevent the humeral cuff 20 from moving down along the patient's arm towards the elbow during use. According to at least one embodiment, and as shown in FIG. 5, a first end 83 of the support strap 82 is secured to a first aperture 85 of an upper or shoulder portion of humeral cuff 20. The support strap 82 extends over the front of the patient's shoulder, behind the patient's neck, down the front of the patient's opposite shoulder, under the armpit of the patient's unbraced arm, and across the patient's back. A second end 84 of the support strap 82 returning along the patient's back is secured to a second aperture 86 of the humeral cuff 20 as illustrated best in FIG. 6. Alternatively, the support strap 82 extends from the back of the upper or shoulder portion of cuff 20, along the patient's back, under the non-braced armpit of the patient, and along the patient's chest to the front side of the upper or shoulder portion of cuff 20.

According to some embodiments, brace 10 is used with, e.g., an elastic, sleeve or liner that is configured to fit snugly over the patient's upper arm prior to application of the brace 10. The sleeve or liner is configured to prevent chafing and fungal colonization on the inner surface of the brace 10. The sleeve can be made of a silver-impregnated material, which is capable of reducing or eradicating the colonization of fungus and/or bacteria. However, the sleeve may be of cotton or any other material known in the art.

In addition, the brace 10 may be used in connection with a sling and/or an abduction pillow known in the art. For example, a support strap may be connected to the forearm cuff 31 or to the humeral cuff 20 and slung over the patient's opposite shoulder in a manner similar to how a sling is donned. An abduction pillow could also be connected to the forearm cuff 31 and/or the humeral cuff 20 to immobilize movement of a patient's arm.

In use, brace 10 is positioned on a patient such that the humeral cuff 20 is appropriately positioned on the upper arm of a patient, as determined by a skilled practitioner based on the type and location of fracture and the type of the brace 10. The angular hinge 50 is located proximate to the fracture site. The range of motion hinge 40 is located at the center of rotation of the patient's elbow, and the forearm cuff 30 is secured to the patient's forearm. To achieve the desired fit, the distance between the humeral cuff 20 and the angular hinge 50 is altered by adjusting the position of the humeral cuff 20 with respect to the upper rigid support 60. Similarly, the distance between the forearm cuff 30 and the range of motion hinge 40 is altered by adjusting the position of the forearm cuff 30 with respect to the lower rigid support 70. According to at least one embodiment, the range of motion hinge 40 and the angular hinge 50 are in a neutral position when the brace 10 is initially secured to a patient.

Once the brace 10 is applied to a patient, x-ray images are obtained. Using the x-ray images, a skilled practitioner measures the angular deformity. Multiple views may be necessary to assess deformity in multiple planes. According to at least one method, a skilled practitioner draws a line down the center of the shaft of each bone fragment and measures the angle between the lines. The angular hinge 50 is adjusted as necessary to account for varus or valgus angulation and to align the distal fracture fragment with the proximal fracture fragment to eliminate or reduce varus or valgus angular deformity, as shown in FIGS. 7A, 7B, 8A and 8B. The angular hinge 50 is adjusted in one embodiment without removing device or brace 10 from the arm of the patient. Additional X-ray images may also obtained as necessary to confirm that angular hinge 50 has been adjusted as necessary to eliminate or reduce varus or valgus angular deformity.

According to at least one embodiment, range of motion hinge 40 is set and/or locked in a neutral position (about 80 or 90 degrees). According to other embodiments, the range of motion hinge 40 may be locked in a position other than neutral as necessary to account for anterior or posterior translation of the distal fragment, and to align the distal fragment with the proximal fragment to eliminate or reduce anterior or posterior angular deformity.

The patient is monitored for proper healing. At some stage of healing, as determined by a skilled practitioner, the range of motion hinge 40 is unlocked and the flexion rotation stop 41 and the extension rotation stop 42 are adjusted to allow for a particular or preset range of motion of the elbow and arm. The flexion rotation stop 41 and the extension rotation stop 42 are further adjusted as necessary to permit movement as deemed appropriate by a skilled practitioner and provide optimal healing of the fracture, while providing some level of ambulation when it is safe and non-painful to do so.

Aspects of the subject matter described herein may be useful alone or in combination with one or more other aspects described herein. Without limiting the foregoing description, in a first aspect of the present disclosure, a device for correcting a bone fracture includes a humeral cuff configured to be secured to a patient's upper arm, a forearm cuff configured to be secured to the patient's forearm, a first hinge pivotally connecting the humeral cuff and the forearm cuff and enabling the forearm cuff to rotate in a first plane relative to the humeral cuff, and a second hinge pivotally connecting the humeral cuff and the forearm cuff and enabling the forearm cuff to rotate in a second plane relative to the humeral cuff.

In accordance with a second aspect of the present disclosure, which can be used in combination with the first aspect, at least one of the first and second hinges can be locked to prevent the forearm cuff from rotating relative to the humeral cuff.

In accordance with a third aspect of the present disclosure, which can be used in combination with any one or more of the preceding aspects, the distance between the humeral cuff or the forearm cuff and the first hinge or the second hinge is adjustable.

In accordance with a fourth aspect of the present disclosure, which can be used in combination with any one or more of the preceding aspects, the adjustable distance is adjusted by a rigid support.

In accordance with a fifth aspect of the present disclosure, which can be used in combination with any one or more of the preceding aspects, the humeral cuff includes at least one shell capable of partially, substantially or completely encircling the upper arm of the patient.

In accordance with a sixth aspect of the present disclosure, which can be used in combination with any one or more of the preceding aspects, one of the first and second hinges is rotatable when the device is applied to the bone fracture, while the other of the first and second hinges is fixed rotationally when the device is applied to the bone fracture.

In accordance with a seventh aspect of the present disclosure, which can be used in combination with any one or more of the preceding aspects, one of the first or second hinges is set to correct a varus or valgus deformity.

In accordance with an eighth aspect of the present disclosure, which can be used in combination with any one or more of the preceding aspects, the humeral cuff includes an upper portion and a lower portion, and the lower portion is adjustable relative to the upper portion so that the lower portion can be secured adjacent to a humeral fracture at a plurality of locations on the patient's upper arm.

In accordance with a ninth aspect of the present disclosure, which can be used in combination with any one or more of the preceding aspects, the first hinge is in mechanical communication with the humeral cuff, the second hinge is in mechanical communication with the forearm cuff, and the first and second hinges are fixedly or adjustably in mechanical communication with each other.

In accordance with a tenth aspect of the present disclosure, which can be used in combination with any one or more of the preceding aspects, a device for correcting a bone fracture includes a humeral cuff configured to be secured to a patient's upper arm, a forearm cuff configured to be secured to the patient's forearm, and a hinge pivotally connecting the humeral cuff and the forearm cuff. The hinge enables the forearm cuff to rotate in a plane that is different than a natural plane of rotation of the patient's elbow.

In accordance with an eleventh aspect of the present disclosure, which can be used in combination with any one or more of the preceding aspects, the hinge is a first hinge and the device includes a second hinge pivotally connecting the humeral cuff and the forearm cuff. The second hinge enables the forearm cuff to rotate in the natural plane of rotation of the patient's elbow.

In accordance with a twelfth aspect of the present disclosure, which can be used in combination with the one or more of the preceding aspects, the first hinge is fixedly or adjustably connected to the second hinge.

In accordance with a thirteenth aspect of the present disclosure, which can be used in combination with any one or more of the preceding aspects, rotation in the different plane allows for correction of a varus or valgus deformity.

In accordance with a fourteenth aspect of the present disclosure, which can be used in combination with any one or more of the preceding aspects, a device for correcting a bone fracture includes a humeral cuff configured to be secured to a patient's upper arm, a forearm cuff configured to be secured to the patient's forearm, and a hinge arrangement connecting the humeral cuff to the forearm cuff. The hinge arrangement enables the forearm cuff to rotate in a plurality of planes relative to the humeral cuff.

In accordance with a fifteenth aspect of the present disclosure, which can be used in combination with any one or more of the preceding aspects, the hinge arrangement can be locked to prevent the forearm cuff from rotating relative to the humeral cuff.

In accordance with a sixteenth aspect of the present disclosure, which can be used in combination with any one or more of the preceding aspects, the hinge arrangement includes a range of motion hinge.

In accordance with a seventeenth aspect of the present disclosure, which can be used in combination with any one or more of the preceding aspects, the hinge arrangement includes an angular hinge.

In accordance with an eighteenth aspect of the present disclosure, which can be used in combination with any one or more of the preceding aspects, a distance between the humeral cuff or the forearm cuff and the hinge arrangement is adjustable.

In accordance with a nineteenth aspect of the present disclosure, which can be used in combination with any one or more of the preceding aspects, the humeral cuff includes first and second portions, and the first portion is adjustable relative to the second portion so that the first portion can be secured adjacent to a humeral fracture at a plurality of locations on the patient's upper arm.

In accordance with a twentieth aspect of the present disclosure, which can be used in combination with any one or more of the preceding aspects, a method of correcting a bone fracture in a patient includes fitting a brace to the patient's arm by locating a humeral cuff on the patient's upper arm and locating a forearm cuff on the patient's forearm, rotating the patient's forearm into a desired position relative to the patient's upper arm, securely fastening the humeral cuff to the patient's upper arm and the forearm cuff to the patient's forearm, and thereafter preventing the patient's forearm from rotating in relation to the patient's upper arm.

In accordance with a twenty-first aspect of the present disclosure, which can be used in combination with any one or more of the preceding aspects, locating the humeral cuff includes adjusting a lower portion of the humeral cuff relative to an upper portion of the humeral cuff so that the patient's bone will be properly compressed.

In accordance with a twenty-second aspect of the present disclosure, which can be used in combination with any one or more of the preceding aspects, a method of correcting a bone fracture in a patient includes selecting an appropriately sized humeral cuff for the patient and attaching the selected humeral cuff to the brace.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A device for correcting a humeral fracture on an upper arm of a patient, wherein an elbow and a forearm distally extend from the upper arm and the upper arm distally extends from a shoulder having a contoured lateral portion, the device comprising:

a humeral cuff including a first shell and a second shell, each having a rigid construction and said first shell having a lower portion and a contoured upper portion, wherein the second shell is positioned opposite the lower portion of the first shell, the second shell and the lower portion of the first shell in combination are adapted to encircle the upper arm of the patient so as to support a corrective compressing of the humeral fracture with the lower portion of the first shell adapted to compress the humeral fracture and the contoured upper portion of the first shell is configured to be secured and conformed to the contoured lateral portion of the shoulder;

a forearm cuff configured to be secured to the forearm;

a first hinge pivotally connecting the humeral cuff and the forearm cuff and enabling the forearm cuff to rotate in a first plane relative to the humeral cuff; and a second hinge pivotally connecting the humeral cuff and the forearm cuff and enabling the forearm cuff to rotate in a second plane relative to the humeral cuff, wherein one of the first and second hinges is adapted to pivot the lower portion of the first shell relative to the forearm cuff to a varus angulation or a valgus angulation that applies pressure to the upper arm and aligns the humeral fracture to eliminate or reduce an angular deformity caused by the humeral fracture, while the other of the first and second hinges is adapted to pivot the first shell relative to the forearm cuff allowing range of motion of the elbow.

2. The device of claim 1, wherein the forearm cuff and the first hinge are separated from one another by a first longitudinal distance and the humeral cuff and the second hinge are separated from one another by a second longitudinal distance, and wherein the first longitudinal distance and/or the second longitudinal distance is adjustable.

3. The device of claim 2, further comprising a lower rigid support connecting the forearm cuff and the first hinge, wherein the first longitudinal distance is adjustable by selectively slidably positioning the lower rigid support along the forearm cuff.

4. The device of claim 2 further comprising an upper rigid support connecting the humeral cuff and the second hinge, wherein the second longitudinal distance is adjustable by selectively slidably positioning the upper rigid support along the humeral cuff.

5. The device of claim 1, wherein the first hinge is a range of motion hinge adapted to pivot the first shell relative to the forearm cuff allowing range of motion of the elbow and the second hinge is an angular hinge adapted to pivot the lower portion of the first shell relative to the forearm cuff to the varus angulation or the valgus angulation that applies pressure to the upper arm and aligns the humeral fracture to eliminate or reduce the angular deformity caused by the humeral fracture.

6. The device of claim 5, wherein the forearm cuff, the range of motion hinge, the angular hinge and the humeral cuff are connectively positioned in series along a length of the device with the forearm cuff more proximal to the range of motion hinge than the angular hinge and the humeral cuff more proximal to the angular hinge than the range of motion hinge.

7. The device of claim 1, wherein the first hinge can be locked to prevent the forearm cuff from rotating in the first plane relative to the humeral cuff about the first hinge.

8. The device of claim 1, wherein the second hinge can be locked to prevent the forearm cuff from rotating in the second plane relative to the humeral cuff about the second hinge.

9. The device of claim 1, wherein one of the first and second hinges is adapted to be selectively rotatable when the device is applied to the humeral fracture, while the other of the first and second hinges is adapted to be selectively fixed rotationally when the device is applied to the humeral fracture.

10. The device of claim 1, wherein the first shell and the second shell are maintained in opposing relation to one another by at least one retention means adapted to adjustably draw the first and second shells toward one another and compress the upper arm.

11. The device of claim 1, wherein the first hinge is configured to be locked to cause the device to function as a splint.

12. The device of claim 1, wherein the first shell is an outer shell adapted to engage a lateral side of the upper arm and the second shell is an inner shell adapted to engage a medial side of the upper arm.

13. A device for correcting a humeral fracture on an upper arm of a patient, wherein an elbow and a forearm distally extend from the upper arm and the upper arm distally extends from a shoulder having a contoured lateral portion, the device comprising:

a humeral cuff having an outer shell and an inner shell positioned in opposing connective relationship to one another and each having a rigid semicircular configuration with a distal end and a proximal end, the outer and inner shells in combination having a tubular configuration, wherein the inner shell is adapted to engage a medial side of the upper arm adjacent to the humeral fracture, the outer shell is adapted to engage a lateral side of the upper arm adjacent to the humeral fracture, the outer and inner shells are adapted in combination to encircle the upper arm to an extent sufficient to support a corrective compression of the humeral fracture and the outer shell is longer than the inner shell with the proximal end of the outer shell extending past the proximal end of the inner shell to define a contoured upper portion of the outer shell adapted to engage the contoured lateral portion of the shoulder;

a forearm cuff configured to be secured to the forearm; and a hinge arrangement connecting the humeral cuff to the forearm cuff, wherein the hinge arrangement enables the forearm cuff to rotate in a plurality of planes relative to the humeral cuff, the hinge arrangement including:

a first hinge pivotally connecting the humeral cuff and the forearm cuff and enabling the forearm cuff to rotate in a first plane relative to the humeral cuff; and a second hinge located between the humeral cuff and the first hinge, the second hinge pivotally connecting the humeral cuff and the forearm cuff and enabling the forearm cuff to rotate in a second plane relative to the humeral cuff, the second hinge configured to pivot the distal ends of the outer and inner shells of the humeral cuff relative to the forearm cuff to apply pressure to the upper arm and align the humeral fracture to eliminate or reduce an angular deformity caused by the humeral fracture.

14. The device of claim 13, wherein the forearm cuff and the hinge arrangement are separated from one another by a first longitudinal distance and the humeral cuff and the hinge arrangement are separated from one another by a second longitudinal distance, and wherein the first longitudinal distance and/or the second longitudinal distance is adjustable.

15. The device of claim 14, further comprising a lower rigid support connecting the forearm cuff and the hinge assembly, wherein the first longitudinal distance is adjustable by selectively slidably positioning the lower rigid support along the forearm cuff.

16. The device of claim 14 further comprising an upper rigid support connecting the humeral cuff and the second hinge, wherein the second longitudinal distance is adjustable by selectively slidably positioning the upper rigid support along the humeral cuff.

17. The device of claim 13, wherein the hinge arrangement can be locked to prevent the forearm cuff from rotating relative to the humeral cuff.

18. The device of claim 13, wherein the first hinge is a range of motion hinge.

19. The device of claim 13, wherein the first hinge is adapted to have a lateral orientation with respect to the patient's arm.

20. A device for correcting a humeral fracture on an upper arm of a patient, wherein an elbow and a forearm distally extend from the upper arm and the upper arm distally extends from a shoulder having a contoured lateral portion, the device comprising:
a humeral cuff having a first shell and a second shell positioned in opposing relationship to one another and each having a rigid configuration with a distal end and a proximal end, wherein the second shell is adapted to engage the upper arm adjacent to the humeral fracture, the first shell is adapted to engage the upper arm adjacent to the humeral fracture and the first and second shells are adapted in combination to encircle the upper arm to an extent sufficient to support a corrective compression of the humeral fracture, and further wherein the first shell is longer than the second shell with the proximal end of the first shell extending past the proximal end of the second shell to define a contoured upper portion of the first shell configured to be secured and conformed to the contoured lateral portion of the shoulder;
a forearm cuff configured to be secured to the forearm;
a first hinge pivotally connecting the humeral cuff and the forearm cuff and enabling the forearm cuff to rotate in a first plane relative to the humeral cuff; and
a second hinge pivotally connecting the humeral cuff and the forearm cuff and enabling the forearm cuff to rotate in a second plane relative to the humeral cuff.

21. The device of claim 20, wherein the first plane is a natural plane of rotation of the elbow.

22. The device of claim 20, wherein the first hinge is fixedly or adjustably connected to the second hinge.

23. The device of claim 20, wherein the second hinge is located between the humeral cuff and the first hinge and is adapted to be positioned on a lateral side of the upper arm and pivot the humeral cuff relative to the forearm cuff to a varus angulation or a valgus angulation that applies pressure to the upper arm and aligns the humeral fracture to eliminate or reduce a varus or valgus deformity.

24. The device of claim 20, wherein the first hinge is configured to be locked to cause the device to function as a splint.

25. A method of correcting a humeral fracture on an arm of a patient, the arm having an upper arm containing the humeral fracture and an elbow and a forearm distally extending from the upper arm, the method comprising:
fitting a brace to the arm by (i) locating a rigid humeral cuff around the upper arm so as to support a corrective compression of the humeral fracture, (ii) locating a forearm cuff on the forearm, (iii) locating a first hinge proximal to the elbow, and (iv) locating a second hinge on a lateral side of the arm;
rotating the forearm into a desired position relative to the upper arm;
securely fastening the rigid humeral cuff to the upper arm and the forearm cuff to the forearm;
pivoting the second hinge to pivot a distal end of the rigid humeral cuff towards a lateral side of the upper arm to apply pressure to the upper arm and align a distal fracture fragment and a proximal fracture fragment on the upper arm; and
preventing the forearm from rotating in relation to the upper arm.

26. The method of claim 25, wherein locating the rigid humeral cuff includes adjusting a lower portion of the rigid humeral cuff relative to an upper portion of the rigid humeral cuff so that the humeral fracture will be properly compressed.

27. The method of claim 25, further comprising selecting the rigid humeral cuff so that the rigid humeral cuff is appropriately sized for the patient and thereafter attaching the rigid humeral cuff to the brace before locating the rigid humeral cuff around the upper arm.

28. The method of claim 25, wherein the second hinge is located between the first hinge and the rigid humeral cuff proximate to the humeral fracture.

29. The method of claim 25, further comprising adjusting the rigid humeral cuff to adjust the corrective compression to the humeral fracture.

* * * * *